United States Patent [19]

Roscher et al.

[11] 4,156,632
[45] May 29, 1979

[54] PROCESS FOR THE SEPARATION OF WATER FROM GAS MIXTURES FORMED IN THE MANUFACTURE OF VINYL ACETATE

[75] Inventors: Günter Roscher, Kelkheim; Heinz Schmitz, Frankfurt am Main, both of Fed. Rep. of Germany

[73] Assignee: Hoechst Aktiengesellschaft, Frankfurt am Main, Fed. Rep. of Germany

[21] Appl. No.: 776,364

[22] Filed: Mar. 10, 1977

[30] Foreign Application Priority Data

Mar. 13, 1976 [DE] Fed. Rep. of Germany ....... 2610624

[51] Int. Cl.$^2$ .............................................. B01D 3/16
[52] U.S. Cl. ........................................ 203/14; 203/98
[58] Field of Search ............... 260/497 A, 497 R, 499; 203/14, 16, 98

[56] References Cited

U.S. PATENT DOCUMENTS

| | | | |
|---|---|---|---|
| 3,404,177 | 10/1968 | Baba et al. | 260/497 A |
| 3,530,043 | 9/1970 | Horn et al. | 203/98 |
| 3,692,636 | 9/1972 | Hugu et al. | 260/499 |
| 3,738,915 | 6/1973 | Fiore et al. | 260/499 |

FOREIGN PATENT DOCUMENTS

586489   3/1947   United Kingdom ..................... 260/499

OTHER PUBLICATIONS

The Condensed Chemical Dictionary –8th ed., Hawley, Van Nostrand Reinhold Co. 1971, p. 926.

Primary Examiner—Hiram H. Bernstein
Attorney, Agent, or Firm—Curtis, Morris & Safford

[57] ABSTRACT

The invention relates to a process for the partial separation of water from gas mixtures formed in the manufacture of vinyl acetate by reaction of ethylene with acetic acid and oxygen in the gaseous phase and in the presence of catalysts. In a "predehydration column", more than half of the water formed in the reaction is eliminated without requiring energy feed. The mixture obtained which is relatively poor in water is worked up according to known methods.

2 Claims, 1 Drawing Figure

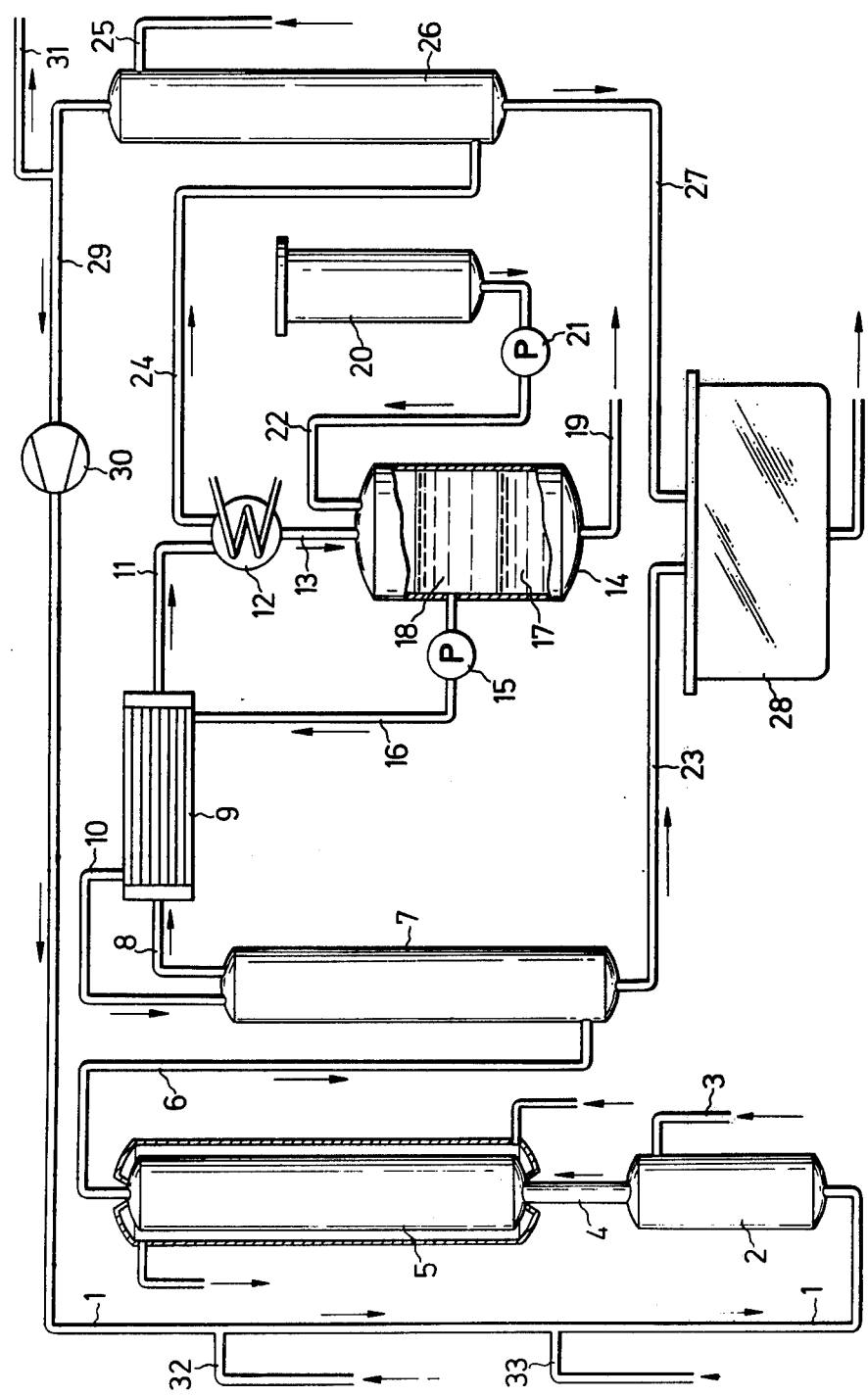

PROCESS FOR THE SEPARATION OF WATER FROM GAS MIXTURES FORMED IN THE MANUFACTURE OF VINYL ACETATE

The manufacture of vinyl acetate by reaction of ethylene with acetic acid and oxygen in the gaseous phase in the presence of fixed bed catalysts is already known. Generally, the reaction proceeds under pressures of from 1 to 25 bars and at temperatures of from 100° to 250° C. The catalysts used in the industrial practice are of different composition; in all cases, however, they contain palladium or palladium salts.

For stoichiometric reasons, one mol of water is formed per each mol of vinyl acetate according to the following scheme:

$$CH_2=CH_2 + \tfrac{1}{2}O_2 + CH_3COOH \rightarrow CH_2=CHOOC.CH_3 + H_2O$$

Since according to the following scheme, part of the converted ethylene is oxidized to $CO_2$ and water $$CH_2=CH_2 + 3O_2 \rightarrow 2CO_2 + 2H_2O,$$

even more than one mol of water is formed per mol of vinyl acetate; generally, the amount of water formed is about one fourth by weight of the amount of vinyl acetate manufactured.

In the industrial manufacturing processes, the hot gas mixture which leaves the vinyl acetate reactor and which is composed of unreacted ethylene, unreacted oxygen, unreacted acetic acid, vinyl acetate, water, $CO_2$ and inert gases such as nitrogen and argon, is generally cooled in several steps, whereby the condensable substances are liquefied. Thus, a liquid mixture is obtained which contains in general about 55 to 75% by weight of acetic acid, 5 to 12% by weight of water, 15 to 35% by weight of vinyl acetate, and small amounts of other components such as ethyl acetate, ethylidene diacetate or acetaldehyde. The uncondensed components are recycled into the reactor.

The liquid mixture may be worked up according to various distillation methods to form pure vinyl acetate and acetic acid, which latter one is recycled into the reaction.

There are several known distillation processes; in one of them, in a first distillation column, a vinyl acetate/water mixture is distilled off at the head. The sump product, substantially acetic acid, of this first column is recycled into the reaction. The distillate is composed of two phases. The organic phase which comprises vinyl acetate — saturated with water — and other low-boiling substances is distilled in a second column; water and low-boiling substances passing over at the head. The sump product of the second column which contains dry vinyl acetate, high-boiling substances and polymers, is separated in a third column into pure vinyl acetate distilling off at the head, and high-boiling substances and polymers which are removed at the bottom.

A further known distillation process operates which two columns only. In the first of these columns, the low-boiling substances, except vinyl acetate, are distilled off at the head. The reflux is removed from a partition plate in the column and passed over a phase separator, where the water is eliminated. The organic phase is then recycled into the column below the partition plate. At the bottom of this first column, a dry mixture of vinyl acetate, acetic acid and high-boiling substances which is free from low-boiling substances is removed. This column is operated under elevated pressure in order to increase the water content in the current discharged from the partition plate, that is, in order to reduce the energy consumption of the column. In the second column, the sump product of the first column containing vinyl acetate, acetic acid and high-boiling substances is separated into pure vinyl acetate which is distilled off at the head, and a sump product containing substantially acetic acid which is recycled into the reaction.

When considering the total energy consumption of these known distillation processes, it is noted that about 60 to 80% of the total energy required for the distillation are consumed for separating the water.

The present invention provides a process which reduces substantially the energy consumption for the dehydration of the crude vinyl acetate mixture by separating part of the water according to a hitherto unknown method before the beginning of the known work-up.

This process for the partial separation of water from gas mixtures formed in the manufacture of vinyl acetate by reaction of ethylene with acetic acid and oxygen in the gaseous phase and in the presence of catalysts, which gas mixtures contain acetic acid, vinyl acetate, water, carbon dioxide and ethylene as main components, comprises introducing the gas mixture escaping from the reaction zone, optionally after previous stepwise cooling, into a distillation column, cooling the mixture escaping in gaseous form at the head of the distillation column to −20° to +50° C., removing the aqueous phase from the condensate formed thereby which separates into two phases, and recycling the organic phase either totally or partially to the column, while removing simultaneously a mixture containing mainly vinyl acetate, acetic acid and water at the bottom of the column.

This latter mixture of vinyl acetate, acetic acid and water discharged from the bottom of the column has a considerably lower content of water than the mixture obtained in the known processes described above, that is, about 2 to 6% by weight instead of 5 to 12% by weight. The use of a "predehydration column" according to this invention allows therefore the elimination of more than half of the water formed in the manufacture of vinyl acetate without requiring special energy in addition.

The mixture of vinyl acetate, acetic acid and water obtained may be worked up according to suitable known methods, for example the two distillation processes described above.

Before introducing it into the predehydration column, the gas mixture leaving the reaction zone is preferably cooled by countercurrent heat exchange using the gas current which is recycled to the acetic acid evaporator and which has a lower temperature. The temperature attained in the gas mixture in this manner depends on the temperature of discharge from the reactor and is between this latter temperature and the lower temperature of the cited circulating gas current.

It was feared that in the operation mode of the invention under the conditions prevailing in the predehydration column, there would be formation of ethylidene diacetate, and of polymers from vinyl acetate, and saponification of vinyl acetate to a large extent. Surprisingly, however, the cited by-products are formed in traces only.

The following advantageous operation mode of the process of the invention is illustrated by the accompanying drawing.

The circulating gas containing ethylene, oxygen and $CO_2$ is introduced via the duct (1) into the acetic acid evaporator (2) designed as bubble column, where acetic acid is added to the gas current via the duct (3). The gaseous mixture leaving the acetic acid evaporator (2) is to the reactor (5) via the duct (4) heated with steam in a jacket (not shown). The reactor (5) consists of a reaction tube having a lenght of 5.60 m and an inner diameter of 32 mm and provided with a jacket. The heat of reaction is dissipated by means of water in this jacket. The reaction tube is packed with catalyst material. The gas mixture leaving the reactor (5) and containing substantially ethylene, acetic acid, vinyl acetate, water, carbon dioxide, oxygen and inert gases such as nitrogen and argon is passed on via the duct (6) to the predehydration column (7) having a length of 2.5 m and a diameter of 50 mm and containing Goodloe packings. The gas mixture leaving the column (7) is forwarded via the duct (8) to the heat exchanger (9), where a countercurrent heat exchange occurs with the reflux which enters via the duct (16) and is fed back via the duct (10) to the column (7). From the heat exchanger (9), the gas mixture is forwarded via the duct (11) to the water-cooled condenser (12) where it is cooled to 20°–25° C. The substances liquefied therein are passed through the duct (13) to the vessel (14), where they are collected. That amount of liquid which exceeds a certain level in the collector vessel (14) is fed back by means of the pump (15) via the duct (16), the heat exchanger (9) and the duct (10) to the predehydration column (7). After a certain time, the condensate in the collector vessel (14) separates into two phases (17) and (18); from that moment on, the aqueous phase (17) is removed via the duct (19), and the organic phase (18) alone is recycled into the prehydration column (7) via duct (16), heat exchanger (9) and duct (10). By means of the pump (21), a stabilizer solution is pumped from the reservoir (20) via the duct (22) into the collector vessel (14). The liquid obtained in the sump of the prehydration column (7) which consists substantially of vinyl acetate, acetic acid and water is removed via the duct (23). The gas mixture leaving the condenser (12) via the duct (24) is liberated from uncondensed vinyl acetate amounts in the washing column (26) charged with acetic acid via the duct (25); the sump product of the column (26) is forwarded via the duct (27) to the vessel (28), where it is united with the sump product of the predehydration column (7) fed in via duct (23) to form "crude vinyl acetate". The residual gas (ethylene, unreacted oxygen and $CO_2$ formed as by-product) leaving the washing column (26) via the duct (29) is recycled via duct (1) and the acetic acid evaporator (2) to the reactor (5) by means of a circulating gas compressor (30). In order to maintain stationary conditions and to eliminate inert gases, a partial current of the circulating gas is discharged as exhaust gas via the duct (31). Fresh ethylene is fed in via the duct (32) and fresh oxygen via the duct (33).

The installation as described above is used in the following example which illustrates the invention.

EXAMPLE

The reactor (5) is charged with 4.4 liters of a known vinyl acetate catalysts which contains 2.3% by weight of palladium, 2% by weight of potassium, 1.9% by weight of cadmium, each in the form of its acetate, on a silicic acid carrier (balls having a diameter of 6 mm). 12 $Nm^3$ (N stands for normal conditions of pressure and temperature) of a mixture which contains about 69% by volume of ethylene, 24% by volume of carbon dioxide and 7% by volume of oxygen is introduced per hour into the acetic acid evaporator (2), to which an amount of acetic acid is fed in such a manner that evaporation of 4.83 kg/h of acetic acid is ensured. The gas entering the reactor is preheated to 155° C. in the duct (4). At the inlet of the reactor (5), an overpressure of 8 atmospheres is established, and the temperature at the outlet of the reactor is adjusted to 160° C. by means of the pressure on the boiling water cooling system in the reactor jacket. The temperature of the gas leaving the reactor, when it enters the predehydration column (7), is 130° C. because of the heat disspation of the duct (6). The gaseous mixture leaving the predehydration column (7) at its head is cooled to 25° C. in the condenser (12). In the vessel (14), 9 kg/h of organic phase (18) are obtained which are fed back via pump (15) and heat exchanger (9) to the predehydration column (7). From the collector vessel (14), 350 g per hour of water containing 3% by weight of vinyl acetate, 0.1% by weight of acetic acid and 0.05% by weight of acetaldehyde are removed. In the sump of the predehydration column (7), where a head temperature of 80° C. and a sump temperature of 90° C. establish themselves, 5 kg/h of a mixture having the following composition are obtained: 60% by weight of acetic acid, 6% by weight of water, 33.8% by weight of vinyl acetate, 0.05% by weight of ethylidene diacetate, 0.1% by weight of acetaldehyde and 0.05% by weight of other high-boiling substances and polymers. For stabilizing purposes, 15 ml/h of a solution of 2.5% by weight of p-benzoquinone in vinyl acetate are pumped into the collector vessel (14).

The residual gas of condenser (12) is fed to the washing column (26), to the head of which 2.9 kg of acetic acid are pumped per hour. In the sump of the washing column (26), 3.8 kg/h of a mixture having the following composition are obtained: acetic acid 76.2% by weight, water 1.4% by weight, vinyl acetate 22.4% by weight, acetaldehyde 0.02% by weight.

The sump product leaving the predehydration column (7) is combined with the sump product of the washing column (26) and the crude vinyl acetate so obtained is passed on to one of the known work-up processes. The gas leaving the washing column (26) is fed back to the acetic acid evaporator (2) via the circulating gas compressor (30). Ethylene and oxygen consumed in the reaction are replaced by fresh ethylene and fresh oxygen fed to the circulating gas. $CO_2$ formed as by-product in the reaction is eliminated from the circulating gas as exhaust gas, and the amount of exhaust gas is adjusted in such a manner that a $CO_2$ concentration of 24% by volume in the circulating gas is maintained.

What is claimed is:

1. A process for the partial separation of water from a gas mixture formed in a manufacture of vinyl acetate by gaseous phase reaction of ethylene with acetic acid and oxygen in the presence of a catalyst in a reaction zone, which gas mixture contains acetic acid, vinyl acetate, water, carbon dioxide and ethylene as main components, comprising: subjecting the gas mixture leaving the reaction zone to stepwise cooling; introducing the gas mixture into a predehydration column; cooling the mixture leaving the head of the column in gaseous form to from −20° to +50° C. to form a condensate having an aqueous phase and an organic phase; removing the aqueous phase and recycling the organic phase either totally or partially to the predehydration column; and removing a mixture containing mainly vinyl acetate, acetic acid and water from the bottom of the column.

2. The process as claimed in claim 1, which comprises recycling unreacted ethylene, unreacted oxygen and carbon dioxide formed in the reaction, after having added acetic acid in an acetic acid evaporator, into the reaction zone.

* * * * *